(12) United States Patent
Göbel (10) Patent No.: US 7,582,098 B2
(45) Date of Patent: Sep. 1, 2009

(54) PERCUTANEOUS GASTROINTESTINAL ANCHORING KIT

(75) Inventor: Fred Göbel, Wilhelmsfeld (DE)

(73) Assignee: Kimberly-Clark Wolrdwide, Inc., Neenah, WI (US)

( * ) Notice: Subject to any disclaimer, the term of this patent is extended or adjusted under 35 U.S.C. 154(b) by 251 days.

(21) Appl. No.: 11/510,888

(22) Filed: Aug. 28, 2006

(65) Prior Publication Data
US 2008/0121553 A1    May 29, 2008

(51) Int. Cl.
  *A61B 17/04* (2006.01)
(52) U.S. Cl. .............. 606/153; 606/192; 604/96.01; 206/439
(58) Field of Classification Search ............... 206/439; 606/153, 192; 604/96.01
See application file for complete search history.

(56) References Cited

U.S. PATENT DOCUMENTS

| | | | |
|---|---|---|---|
| 3,253,594 A | 5/1966 | Matthews et al. | |
| 3,397,699 A | 8/1968 | Kohl | |
| 4,077,412 A | 3/1978 | Moossun | |
| 4,315,513 A | 2/1982 | Nawash et al. | |
| 4,393,873 A | 7/1983 | Nawash et al. | |
| 4,516,968 A | 5/1985 | Marshall et al. | |
| 4,666,433 A | 5/1987 | Parks | |
| 4,668,225 A | 5/1987 | Russo et al. | |
| 4,677,967 A | 7/1987 | Zartman | |
| 4,685,901 A | 8/1987 | Parks | |
| 4,769,004 A | 9/1988 | Poindexter | |
| 4,861,334 A | 8/1989 | Nawaz | |
| 4,986,810 A | 1/1991 | Semrad | |
| 5,073,166 A | 12/1991 | Parks et al. | |
| 5,112,310 A * | 5/1992 | Grobe ........................ 604/175 |
| 5,183,464 A | 2/1993 | Dubrul et al. | |
| 5,232,440 A | 8/1993 | Wilk | |
| 5,234,454 A * | 8/1993 | Bangs ........................ 606/191 |
| 5,267,968 A | 12/1993 | Russo | |
| 5,273,529 A | 12/1993 | Idowu | |
| 5,275,610 A | 1/1994 | Eberbach | |
| 5,279,564 A | 1/1994 | Taylor | |
| 5,290,249 A | 3/1994 | Foster et al. | |
| 5,318,542 A | 6/1994 | Hirsch et al. | |
| 5,356,391 A | 10/1994 | Stewart | |
| 5,358,488 A | 10/1994 | Suriyapa | |

(Continued)

FOREIGN PATENT DOCUMENTS

EP    1025802 A1    8/2000

(Continued)

Primary Examiner—Bryon P Gehman
Assistant Examiner—Ernesto A Grano
(74) Attorney, Agent, or Firm—Sue C. Watson; Scott B. Garrison (57) ABSTRACT

The invention describes a percutaneous gastrointestinal anchoring kit having an anchor, an introducer, a guide, an inflator, and a retainer. The anchor contains a ballooned region and a shaft portion. The retainer secures the anchor within the stomach when the ballooned region is inflated by seating against an exterior surface of the patient body and placing a tractive force on the ballooned region so as to pull the gastric lumen to an interior abdominal wall of the patient body. The introducer is used to insert the anchor initially within the stomach. The guide positions the ballooned region of the anchor within the stomach by enabling manipulation from an exterior surface of the patient body. The inflator is used to selectively inflate or deflate the ballooned region as needed.

11 Claims, 8 Drawing Sheets

U.S. PATENT DOCUMENTS

| | | | |
|---|---|---|---|
| 5,431,676 A | 7/1995 | Dubrul et al. | |
| 5,439,444 A * | 8/1995 | Andersen et al. | 604/102.02 |
| 5,443,449 A | 8/1995 | Buelna | |
| 5,484,420 A | 1/1996 | Russo | |
| 5,507,279 A * | 4/1996 | Fortune et al. | 128/200.26 |
| 5,549,657 A | 8/1996 | Stern et al. | |
| 5,860,960 A | 1/1999 | Quinn | |
| 6,039,714 A | 3/2000 | Cracauer et al. | |
| 6,090,073 A * | 7/2000 | Gill | 604/164.01 |
| 6,186,985 B1 | 2/2001 | Snow | |
| 6,322,538 B1 | 11/2001 | Elbert et al. | |
| 6,387,076 B1 | 5/2002 | Landuyt | |
| 6,402,722 B1 | 6/2002 | Snow et al. | |
| 6,458,106 B1 | 10/2002 | Meier et al. | |
| 6,471,676 B1 | 10/2002 | Delegge et al. | |
| 6,482,183 B1 | 11/2002 | Pausch et al. | |
| 6,582,395 B1 | 6/2003 | Burkett et al. | |
| 6,673,058 B2 | 1/2004 | Snow | |
| 6,743,207 B2 | 6/2004 | Elbert et al. | |
| 6,765,122 B1 | 7/2004 | Stout | |
| 6,769,546 B2 * | 8/2004 | Busch | 206/571 |
| 7,264,609 B2 | 9/2007 | Hakky et al. | |
| 2002/0169360 A1 | 11/2002 | Taylor et al. | |
| 2004/0092796 A1 | 5/2004 | Butler et al. | |
| 2004/0097794 A1 | 5/2004 | Bonutti | |
| 2004/0193114 A1 | 9/2004 | Elbert et al. | |
| 2005/0216040 A1 | 9/2005 | Gertner et al. | |
| 2005/0267520 A1 | 12/2005 | Modesitt | |

FOREIGN PATENT DOCUMENTS

| | | |
|---|---|---|
| EP | 1077057 B1 | 7/2004 |
| WO | WO 97/25095 | 7/1997 |
| WO | WO 98/19730 | 5/1998 |
| WO | WO 98/26720 | 6/1998 |
| WO | WO 00/50110 | 8/2000 |
| WO | WO 03/094826 | 11/2000 |
| WO | WO 02/058594 | 8/2002 |
| WO | WO 02/066108 | 8/2002 |
| WO | WO 03/092780 | 11/2003 |
| WO | WO 2005/110280 | 11/2005 |

* cited by examiner

PERCUTANEOUS GASTROINTESTINAL ANCHORING KIT

BACKGROUND OF THE INVENTION

The present invention relates to pre-packaged surgical kits in general, and more particularly to surgical kits for percutaneous gastrointestinal anchoring procedures or a gastropexy kit.

Various medical procedures are simplified by providing the physician with a kit that contains the majority, if not all, of the necessary medical articles that the physician will need to complete a particular procedure. Kits may include articles such as, for example, drapes, syringes, scalpels, needles, clamps, gauze, sponges, drugs, sutures, and devices. Such kits are commonly provided for procedures such as, for example, percutaneous endoscopic gastrostomy ("PEG") and laparoscopic jejunostomy. These kits reduce the time spent by hospital personnel gathering the appropriate articles that are required for a particular procedure and ensure that the surgeon has each article at hand at the appropriate point in the procedure.

A PEG procedure is utilized to place a feeding tube into a patient that extends from the interior of the patient's stomach exteriorly of the patient. The feeding tube permits nutrients to be placed directly into a patient's stomach. This may be necessary when a patient has a disorder of the gastrointestinal tract, malabsorption (impaired absorption of nutrients, vitamins or minerals from the diet by the lining of the small intestine), or neurological or renal disorders. The feeding tube inserted using a PEG procedure is kept in place until a stoma is formed. Once a stoma is formed, the PEG feeding tube may be removed and replaced with an alternate feeding device.

Prior to placement of any feeding tube, it has been found that it is particularly desirable to anchor the anterior wall of the stomach to the abdominal wall as a step prior to creating the stoma tract through the two. Thus attachment has been found to be critical as it helps to prevent inadvertent separation and exposure of the peritoneal cavity to contamination and possible peritonitis.

Typically a T-shaped fastener or anchor is percutaneously introduced into the gastric lumen or stomach. This fastener consists of wire or other filament affixed to a small metal bar or rod. The point at which the two are conjoined is at the center of the bar. The overall visual look of the device is that of the letter "T", with the wire forming the vertical component and the bar forming the horizontal or cross component. The device is typically loaded into an introducer needle or the like with the rod pivoted at the connection with the wire so that the two are essentially in alignment. The introducer is inserted into the stomach, the wire pushed distally from the introducer until the horizontal bar is deployed at which time it at least partially pivots into the T-configuration. The introducer is retracted from the stomach and a tractive force is applied to the wire, the T-component seats against the wall of the stomach and continued pulling serves to draw the anterior wall of the stomach to the abdominal wall.

Although these devices perform the function that they are designed for, a number of problems do exist with them. Typically the T-shaped fastener or horizontal T-bar is not removable back through the incision. As such once the procedure has been completed and the device ready to be removed, the wire is typically cut and the T-bar is left in the body cavity where it is allowed to pass naturally in the patient's stool. In many cases the T-bar is not passed and remains within the body cavity. Consequently, in many cases these initial placement devices are often not readily removable without additional invasive surgical procedures. This is further complicated by the fact that during the six to eight weeks it takes for the fistula's stoma tract to be established, the anchoring mechanism i.e., the small metal T-shaped fastener may embed itself into the gastric or intestinal wall and ultimately lead to infection. Furthermore, the edges of the T-bar often irritate the stomach lining which can be uncomfortable for the patient. Although these devices are often formed of stainless steel, hydrochloric acid contained within the gastric juices of the patient may cause some minor erosion to the device due to the time in which the device is maintained in place.

As described above, in order to achieve the desired seal between the stomach and the abdominal wall, a tractive force must be applied to the anchoring mechanism. This force is applied in such a way so as to pull the stomach cavity to the abdominal wall in order to induce the penetration through the tissue layers to fuse or heal together thus creating the passage or stoma leading from the patient's stomach to an external environment. Accordingly, it is necessary to apply this tractive force for a period of a couple of days through a couple of weeks until the stoma site adequately heals. During this period the patient has reduced mobility which may lead to additional post-operative complications.

While gastropexy devices do exist, there is a need and desire for a gastropexy kit which provides all of the components necessary to enable percutaneous gastrointestinal anchoring prior to the placement of a feeding tube in the patient. Such a kit would prove useful in fostering the permanent fusion of the stomach wall to the abdomen. A less traumatic anchoring system provided in such a kit could serve to reduce the invasiveness of the procedure, to greatly enhance wound healing, to enable immediate, post-placement gastric access for feeding and drainage, and ultimately to allow for the atraumatic removal of the anchoring system. As such what is needed is a kit containing an anchoring or fixation device that is easy to place within an internal body cavity, allows for the formation of a stoma between the internal body cavity and the external environment without significantly impacting the patient's mobility, and enables the clinician to easily remove the fixation device when it is no longer necessary.

SUMMARY OF THE INVENTION

In response to the foregoing problems and difficulties encountered by those of skill in the art, the present invention is directed toward a percutaneous gastrointestinal anchoring kit having an anchor, an introducer, a guide, an inflator, and a retainer. The anchor contains a ballooned region at a distal end of the anchor and a shaft portion extending from the ballooned region to a proximal end of the anchor. The introducer traverses the body tissue layers from an exterior surface of a patient body to the stomach and inserts the anchor within the stomach. The guide positions the ballooned region of the anchor from the bore into the gastric lumen while enabling the proximal end of the anchor to be manipulable at an exterior surface of the patient body. The inflator is used to introduce a fluid into or remove a fluid from the anchor so as to selectively inflate or deflate the ballooned region within the gastric lumen. The retainer secures the anchor within the gastric lumen when the ballooned region is inflated by seating against the exterior surface of the patient body and placing a tractive force on the ballooned region so as to pull the gastric lumen to an interior abdominal wall of the patient body.

In another embodiment, the invention is directed toward an apparatus for insertion into a body orifice for anchoring a first body tissue layer to a second body tissue layer. In a first embodiment, a sheath having a longitudinal bore therethrough is provided. The sheath has a proximal end and a distal end, the distal end is adapted for insertion through at least two body tissue layers and into a body orifice from a point exterior to the body orifice. A hollow preshaped microthin polymeric device is used with the sheath the device contains a shaft and a ballooned region located at or proximal to a distal end of the device. The device slidably engages the bore of the sheath such that the distal ends of each are proximate to one another. While they are engaged, the retention element is in a first collapsed state. A second free end of the device protrudes from the proximal end of the sheath. The device is adapted to be slid distally through the bore until at least the retention element is free of the sheath whereupon an inflation source may be applied to the device ballooning the retention element into a second expanded state.

Such an apparatus may utilize a device made wholly or partially of a polyurethane material. The sheath may be longitudinally splittable into two or more sections along a longitudinal separation line. Other embodiments may use a non-splittable sheath having a slot or groove at a distal end for the capture of the retention element therein. A retainer for affixing to a portion of the shaft protruding from the body to retain the apparatus in position may also be provided.

In another embodiment, an apparatus for insertion into a body orifice for anchoring a first body tissue layer to a second body tissue layer would have a hollow, collapsible, microthin polymeric shaft affixed to a noncollapsible tip at a distal end of the polymeric shaft. A preformed balloonable distention formed in a discrete region of the shaft proximal to the noncollapsible tip would be adapted to anchor against one of the body tissue layers within the body orifice. A rod may be attached at one end to the tip, allowed to extend along the shaft and terminate at a second end near a proximal end of the device. The rod would be adapted to transfer movement from the second end to the first end so as to effect a movement in the tip. The rod may be wholly or partially located internal to the shaft, external to the shaft, and/or within the shaft wall. This apparatus may have a proximally facing flattened surface on the balloonable distention located substantially normal to a longitudinal axis through the shaft.

A method for anchoring a first body tissue layer to a second body tissue layer would encompass the following steps: inserting a distal end of a longitudinally splittable sheath having a throughbore into a body through at least a first body tissue layer, a second body tissue layer, and into a body cavity, leaving a proximal end of the sheath protruding externally from the body; advancing a hollow preshaped microthin polymeric device having a shaft with a ballooned region integrated into a distal end of the shaft along the throughbore until the retention element protrudes from the distal end of the sheath; ballooning the retention member by inflating the member so that it expands from a first deflated condition to a second inflated condition; withdrawing the sheath from the body and sliding it free from the polymeric shaft at a proximal end of the shaft; and pulling the first and second body tissue layers one toward the other by applying a tensile force to the shaft so that the retention member contacts and draws one body tissue layer toward the other body tissue layer.

Another method may encompass the steps of perforating the first and second body tissue layers to create a stoma extending from a first region to a second region within a body orifice; advancing a hollow preshaped microthin polymeric device having a shaft with a ballooned region integrated into a distal end of the shaft into the body orifice by manipulating a rod attached at the distal end and extending to a proximal end until the ballooned region is situated; ballooning the retention member by inflating the member so that it expands from a first deflated condition to a second inflated condition; and pulling the first and second body tissue layers one toward the other by applying a tensile force to the shaft so that the retention member contacts and draws one body tissue layer toward the other body tissue layer.

Additional steps may include by itself or in any combination, the following: tying off an end of the shaft which protrudes externally from the stoma; engaging an end of the shaft which protrudes externally from the stoma with a thin retainer adapted to secure the protruding shaft proximal to the perforation; and/or bandaging the protruding shaft and retainer.

The apparatus and methods described herein would be suitable for use in performing a gastropexy procedure wherein one of the body tissue layers comprises the abdominal wall and the other layer comprises the stomach. Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

Reference will now be made in detail to embodiments of the invention, one or more examples of which are illustrated in the figures. The embodiments are provided by way of explanation of the invention, and not meant as a limitation of the invention. For example, features illustrated or described as part of one embodiment may be used with another embodiment to yield still a different embodiment. It is intended that the invention include these and other modifications as come within the scope and spirit of the invention.

In response to the foregoing challenges that have been experienced by those of skill in the art, the present invention is directed toward a kit for performing percutaneous gastrointestinal anchoring of the anterior wall of the stomach to an anterior wall of the abdomen. Components within such a kit would enable the incising of an exterior surface of a living body, the introduction of an anchoring device into the incision from the exterior surface through intervening tissue layers and into the stomach cavity or gastric lumen. Moreover, components within the kit would enable the application of a tractive force to be applied resulting in the anchoring of the tissue layers and the ultimate formation of an artificial stoma or stomas into or within the living body.

As such, an embodiment of a percutaneous gastrointestinal anchoring kit 10 according to the invention is illustrated in the figures. The kit 10 may include a tray 12 having a plurality of planar surfaces and a plurality of recesses that may be disposed within the planar surfaces. The tray 12 may be formed of any suitable material, for example the tray 12 may be molded from a transparent or translucent substantially rigid plastic material (i.e., PETG). The plurality of recesses would be adapted to hold articles or implements that are useful in performing the procedure. Each recess may be adapted to hold one or more articles. Articles found useful and placed in the recesses are discussed in greater detail below. The recesses may also include detents, protrusions, or the like to frictionally engage the articles and positively retain them within the respective recesses.

Figure 1:
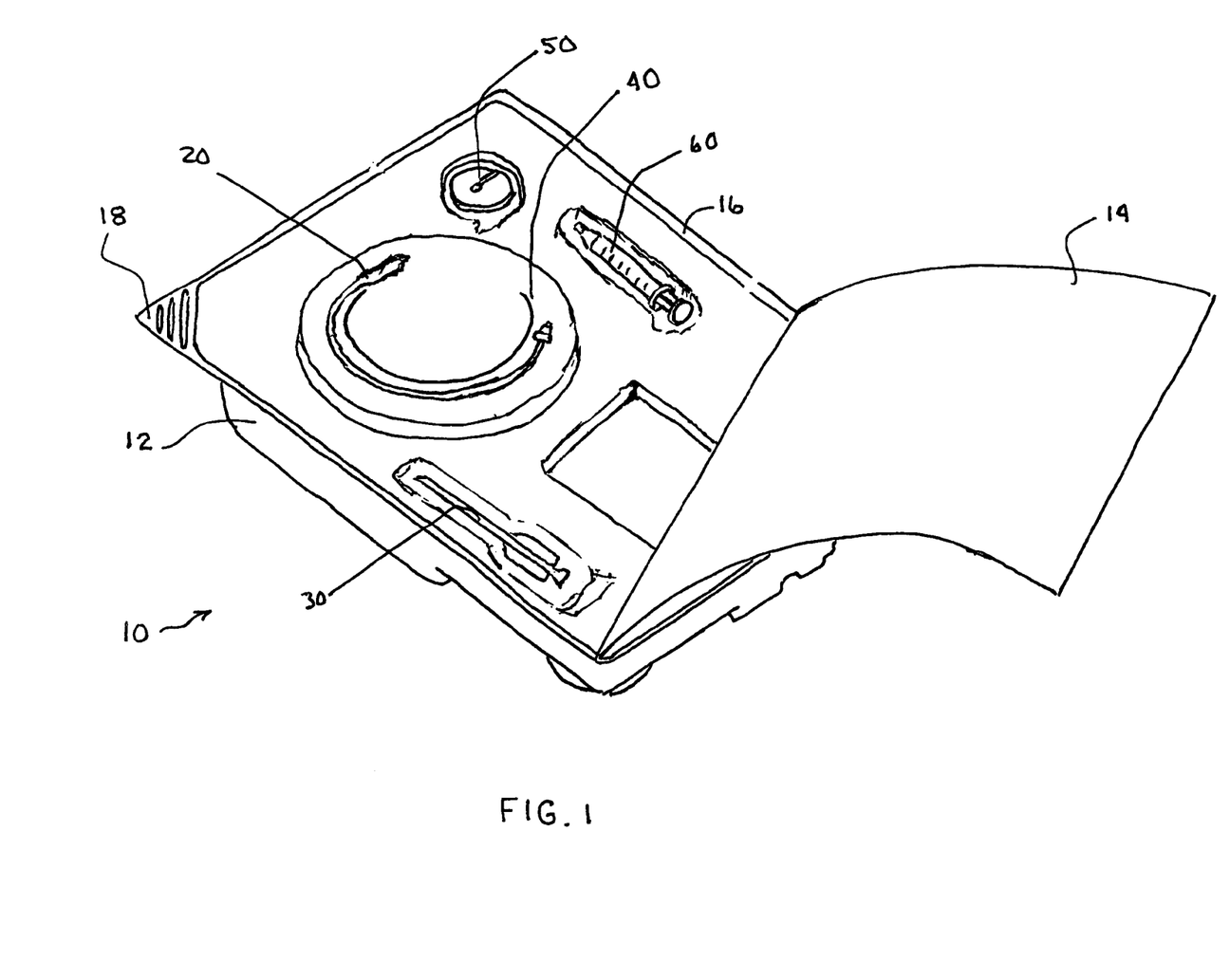
FIG. 1 depicts an illustrative view of one embodiment of the present inventive kit for use in a percutaneous gastrointestinal anchoring procedure.

As seen in FIG. 1, a cover 14 may be positioned on the tray 12 and, in some embodiments, may be adhered to a relatively flat peripheral surface 16 of the tray 12. A corner 18 of the tray 12 may be configured so that a portion of the cover 14 is not adhered to the corner 18. In such an embodiment, a user may grasp the cover 14 that is positioned adjacent to the corner 18 to remove the cover 14 from the tray 12. The cover 12 may be attached to the tray by any suitable method, including adhesives, heat sealing, sonic or thermal welding, solvents, etc. Once all of the articles have been placed into the tray 12 and the cover 14 sealed to the tray, the kit 10 may be subjected to ETO (ethylene oxide) gas sterilization. For this reason, the cover 12 is gas permeable. A suitable cover material is Tyvek®, a spunbond polyolefin, from DuPont of Wilmington, Del. Any number of other permeable web materials suitable for ETO gas sterilization, such as Kraft paper, may be used as the cover 12.

In the kit 10 depicted in FIG. 1, the following articles are contained: an anchor 20, an introducer 30, a guide 40, a retainer 50, and an inflator 60. Additional articles (not shown) any of which may be provided may include an instruction pamphlet, a surgical drape, ointments, swab sticks, bandages, clamps, hemostats, various needles, tape, sterile gauze, scalpels, and a local anesthetic.

Figure 2:
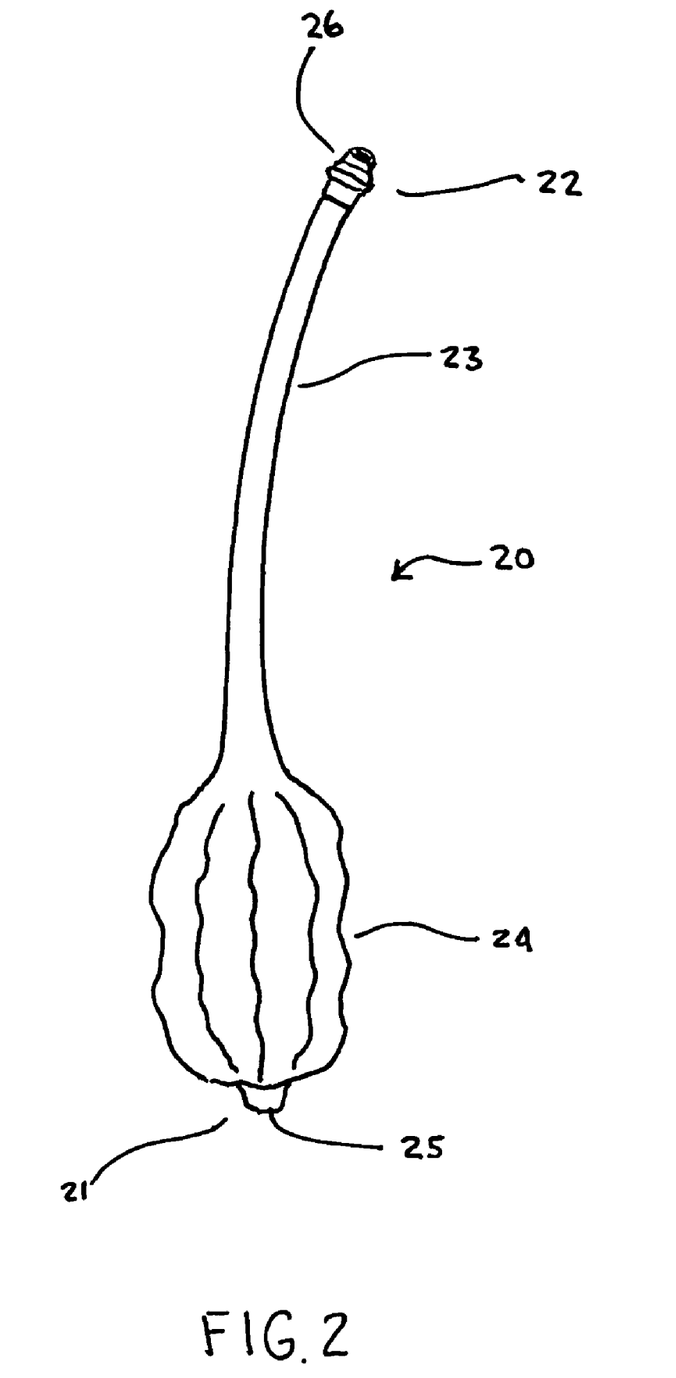
FIG. 2 depicts an illustrative view of the anchor of the FIG. 1 kit in greater detail.

FIG. 2 depicts the anchor 20 in greater detail. The anchor 20 is adapted for insertion into the stomach cavity and serves to anchor an anterior wall of the gastric lumen to an anterior wall of the abdomen for the purpose of drawing the two walls together into intimate contact so as to fuse one to the other. In one simple embodiment, the anchor 20 is provided with a distal end 21 and a proximal end 22. As used herein, distal refers generally to the direction of the patient, while proximal refers to the direction of the user. The anchor 20 is formed of a biocompatible polymeric material configured as a hollow shaft 23 with a ballooned region 24 at or near the distal end 21.

According to some embodiments the material selected to form the anchor 20 may include polyurethane (PU), low-density polyethylene (LDPE), polyvinyl chloride (PVC), polcyamid (PA) or polyethylene teraphthalate (PETP), These materials are biocompatible and, when being processed into correspondingly thin walls, are especially suited for forming the ballooned region 24. Copolymer admixtures for modifying the characteristics of the material are also possible, for example a low density polyethylene and ethylene-vinylacetate copolymer (LDPE-EVA), or blends of the above mentioned materials (e.g. PU with PVC or PU with PA) would be considered suitable for such a device. Other materials would also be suitable so long as they exhibit properties enabling them to be processed into anchor mechanisms having microthin walls which do not deform elastically to such a degree that they are enabled to slip through the insertion channel in the body wall.

Formation of the ballooned region 20 may be achieved by situating the shaft 23 at an appropriate position in a suitable mold (not shown), applying heat and expanding the heated region of the shaft controllably, typically by inflating the heated region within the heated mold. This process enables the discrete region to be distended without otherwise damaging the shaft. Due to the controlled distention of the region forming the ballooned region, the wall thickness is characteristically reduced in that area. Stretching the region during this process serves to molecularly align the polymeric chains thus making the product otherwise stronger than it would be even at microthin wall thicknesses. Such techniques would be known and understood by those of skill in the art.

Final wall thicknesses for the ballooned region 20 are considered to be microthin in nature, and may range from about 25 microns down to about 3 microns whereas the shaft wall thicknesses may range from about 50 microns to about 150 microns. As seen in FIG. 1, the ballooned region 20 is not elastically distendable but is preformed and exists in a collapsed condition when not inflated.

During the manufacturing process for the device, the distal end 21 would be blocked, sealed, or otherwise made fluid tight. Although the distended region or ballooned region 20 may be situated at the distal end 21, it may alternatively be proximal to the distal end such that the anchor 20 at the distal end 21 terminates in a nipple or tip 25. This tip 25 may also be made non-collapsible by the filling of the tip 25 with a potting compound such as a polymer, for example, silicone or the like, or another biocompatible material. This would provide a degree of rigidity to the distal end 21 of the anchor 20 and may be desirable in some embodiments.

The ballooned region 24 of the anchor 20 is adapted to be inflated and deflated. Inflation allows the anchor 20 to perform its function as described below whereas deflation allows the anchor 20 to be inserted and/or removed from the patient, also as described below. To enable the selectable inflation/deflation of the ballooned region 24, a connector 26 may be situated at or near the proximal end 22 of the anchor 20. The connector 26 would be capable of engaging the inflator 60. Suitable connectors may include luer fittings and the like and are known and understood by those of skill in the art.

In some embodiments, the connector 26 may comprise a releasable one-way valve disposed at the proximal end 22 of the anchor 20. Appropriate valves capable of serving in this function are known and their incorporation into the anchor 20 would prevent inadvertent deflation once the inflator was removed from the connector. Such devices are well known in the medical field and would be understood by those having skill in the art. These valves are suitable for actuation by means of the inflator 60 itself. Consequently, it would be understood that such a valve would serve as a means to control the injection of fluids into or the removal of the same from the anchor 20. As would be apparent, control of the inflation of the anchor 20 enables the user or a physician, etc., to selectively control inflation and deflation of the ballooned region 20.

Figure 3:
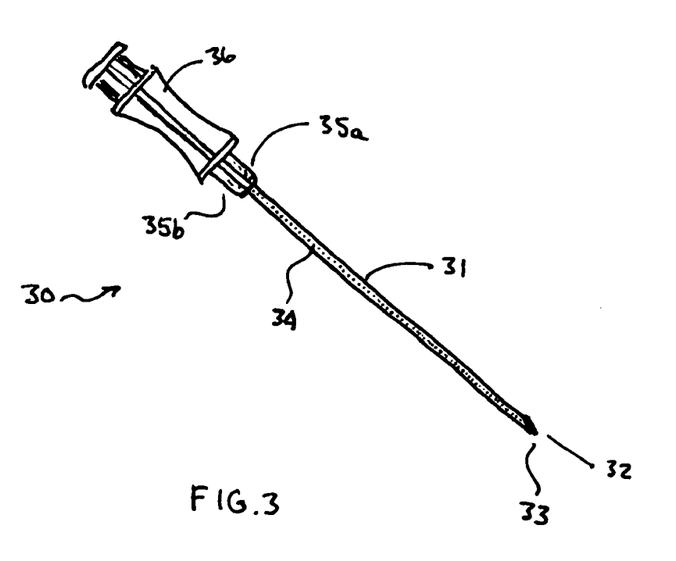
FIG. 3 depicts an illustrative view of the introducer of the FIG. 1 kit in greater detail.

FIG. 3 depicts the introducer 30 in more detail. The introducer 30 is adapted to ultimately place and deploy the anchor 20 within the gastric lumen. In the FIG. 3 embodiment, for example, the introducer is configured as a sheath 31 having a longitudinal bore 32 extending axially along its length. The anchor 20 resides within the bore 32 and is subsequently deployed therefrom. It should be understood that the introducer 30 may simply consist of the sheath 31 which must be introduced into the gastric lumen by means of an incision performed by the clinician with a scalpel or separate introducer needle. However, as depicted in this embodiment, the sheath 31 may actually be used as the introducer needle itself for perforating the tissue and creating a stoma into the gastric lumen or stomach cavity. In those instances where the sheath 31 serves as the needle, a trocar tip 33 may be desirable. The trocar tip would be adapted to penetrate the tissue. Depending upon the size of the sheath 31 in comparison to the location of the connector 26 situated on the anchor 20, removal of the sheath 31 from the anchor may be difficult. As such, the sheath 31 may be longitudinally splittable along a separation line 34 and removable from the anchor in at least two longitudinally discrete parts 35a and 35b. A pair of wings 36 would be provided for grasping and initiating separation of the parts 35a and 35b. Those of skill in the art would understand how the separation line is formed by etching or perforating the sheath longitudinally along its axis.

Figure 4:
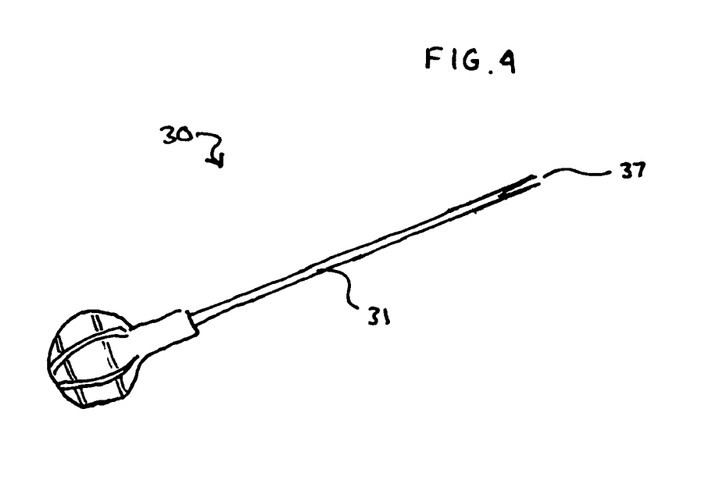
FIG. 4 depicts an illustrative view of an alternative embodiment of the FIG. 3 introducer.

FIG. 4 depicts an alternate version of the introducer 30. In this embodiment, the sheath 31 contains a groove or slot 37 machined into the sheath 31. The slot 37 would be adapted to engage a portion of the anchor 20. In this embodiment, the anchor 20 may or may not be situated internal to the introducer 30 and may actually be laid alongside the introducer 30 when it is inserted into the stomach. In this way, the introducer 30 may be removed without splitting the sheath 31. For example, a guide described in more detail below may be provided with a detent 43 depicted in FIG. 6, the detent 43 is designed to be captured in the slot 37.

In either described embodiment, the anchor 20 should be capable of deployment and inflation without risk of puncture or damage. This is especially of concern in those embodiments having the trocar tip 33. For this purpose, the guide 40 is provided. The guide 40 serves as a rigid or semi-rigid linkage or connection between the nipple or tip 25 and a point proximal the proximal end 22 of the anchor 20. The guide is adapted to be physically grasped at one end and manipulated by a clinician. The guide 40 would prove useful in pushing the ballooned region 24 out of the introducer 30 prior to inflation of the ballooned region 24. As such, it would be simple to ensure that the ballooned region 24 be located at a puncture safe distance from the trocar tip 33 yet be placed close to its ultimate location. At that time the introducer 30 may be removed from the body and the ballooned region 24 inflated.

Figure 5:
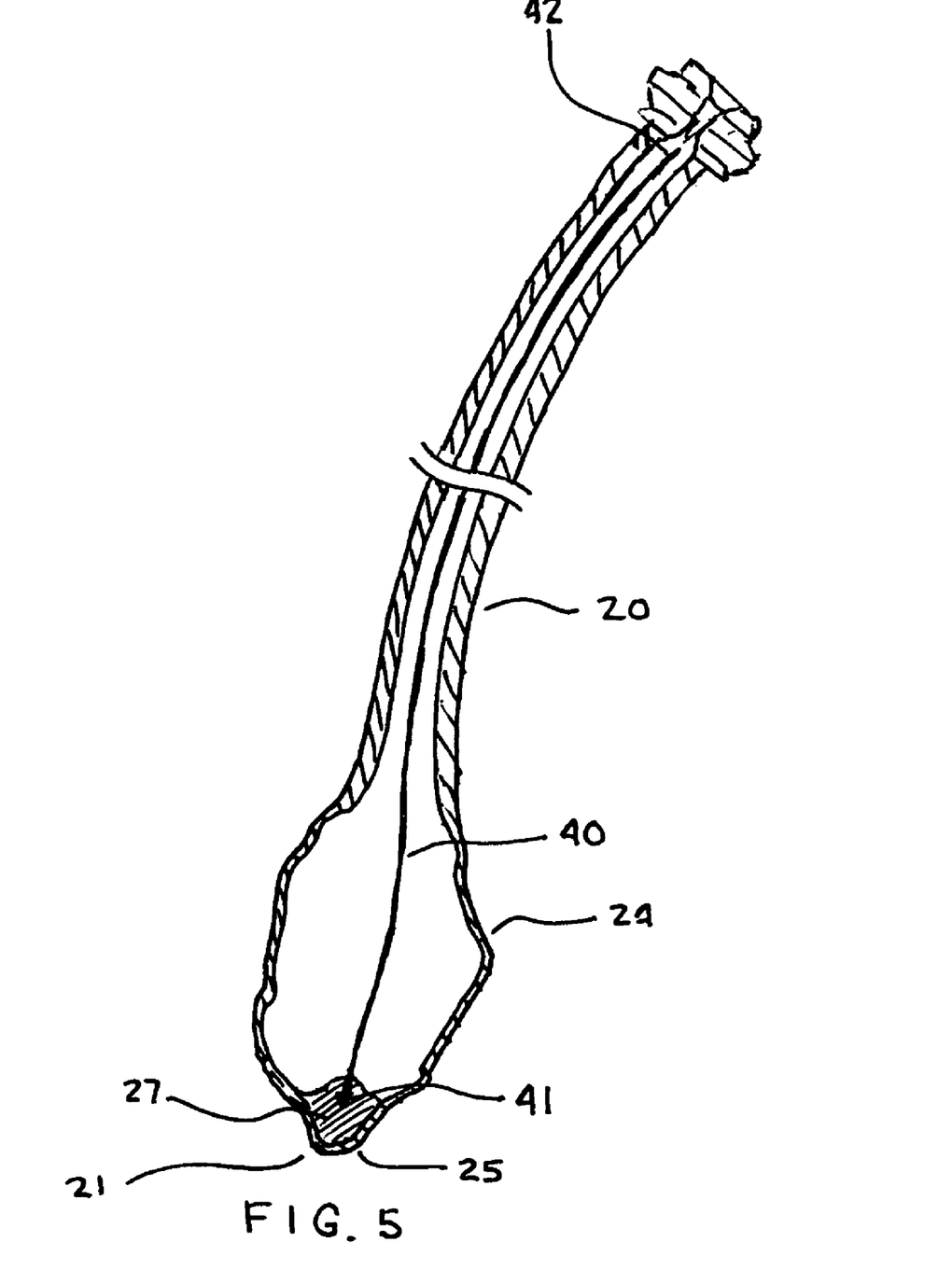
FIG. 5 depicts an illustrative view of the guide of the FIG. 1 kit in greater detail.

The guide 40 may be made of any number of rigid or semi-rigid constructs, including a rod, wire, shaft, tube, or thin bar. Turning now to FIG. 5, it may be seen that the guide 40 is affixed at a first end 41 to the distal end 21 of the anchor 20. In many cases, the end 41 is embedded in a potting compound 27 contained within the distal end 21, typically in the tip 25. A second end 42 is provided near the proximal end 22 of the anchor 20 as stated. This second end 42 would be accessible to a clinician even should the ballooned region 24 of the anchor 20 be situated within the body of the patient. Due to the thin walls of the anchor 20, even though the guide 40 is within the interior of the anchor 20 it should still be manipulable from the exterior of the anchor 20.

As stated, the first end 41 of the guide 40 may be bedded within the potting compound 27 contained within an interior of the anchor 20, in many instances, the tip 25. Although the potting compound would not normally be accessible to the body, in most instances it likely would comprise a biocompatible material such as silicone. Regardless of the material used, the potting compound should be capable of capturing one end 41 of the guide 40 at least with respect to a pushing force. By forming this linkage or connection, it would be understood that any force applied to the one end 42 of the guide 40 is transferred to the other end 41 without buckling. The clinician by manipulating the guide 40 could effect the position of the ballooned region 24 within the patient.

Earlier, the guide 40 was described as being seated within a potting compound 27 and captured at least with respect to a pushing force. That phrase is meant to indicate that the potting compound will encompass or otherwise contain the guide 40, enable the guide to be pushed into the newly created stoma, while minimizing the likelihood that the guide will inadvertently be pushed through the potting compound and ultimately puncture or otherwise breach the integrity of the distal end 21 of the anchor 20. In some embodiments the guide 40 may be removable from the anchor 20 once the ballooned region 24 is in place. Alternatively, the guide 40 may be made sufficiently flexible so as not to interfere with a clinician's ability to tie a trailing end of the shaft 23 which protrudes from the body of the patient. For example, if the guide 40 were wire-like, in some cases it may remain in place and not interfere with the tying process and may even prove useful in assisting with the tying of the shaft so as to be fluid tight.

The guide 40 in many embodiments, like that of FIG. 5, may be situated internally to the anchor 20 through the shaft 23 and as such, would extend along the length of the anchor 20. In such embodiments, the guide 40 would be sized so as not to completely occlude the inflation and deflation features of the ballooned region 24. In some embodiments, the guide 40 would be sized such that its cross-sectional area was between about one-third to about two-thirds of the cross-sectional area of the inside diameter of the shaft 23.

Figure 6:
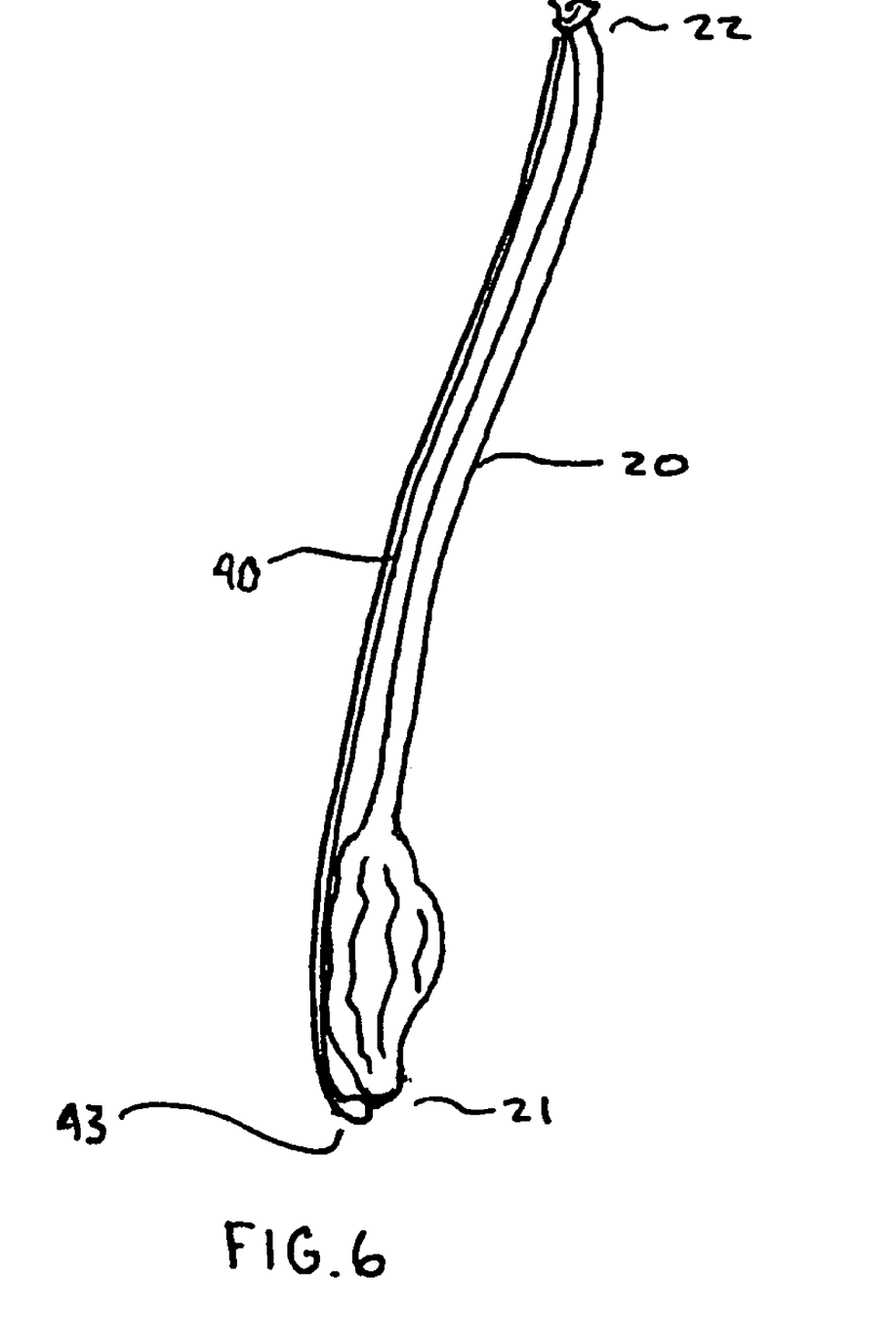
FIG. 6 depicts an illustrative view of an alternative embodiment of the FIG. 5 guide.

Although many of the embodiments described place the guide 40 within the anchor 20 and shaft 16, this is not a requirement for any of the embodiments. In fact, as depicted in FIG. 6, the guide 40 may run along an exterior surface of the anchor 20 or be placed within a wall of the anchor 20 itself. In any event, it should not be lost sight of that the purpose of the guide is to enable placement of the anchor 20 within the patient and allow manipulation of the ballooned region 24. By articulating or otherwise moving the guide 40 at or near the proximal end 22 of the anchor 20, which would be external to the patient once the anchor 20 is in place, the articulation is transferred through the anchor 20 from the proximal end 22 to the distal end 21.

Figure 7:
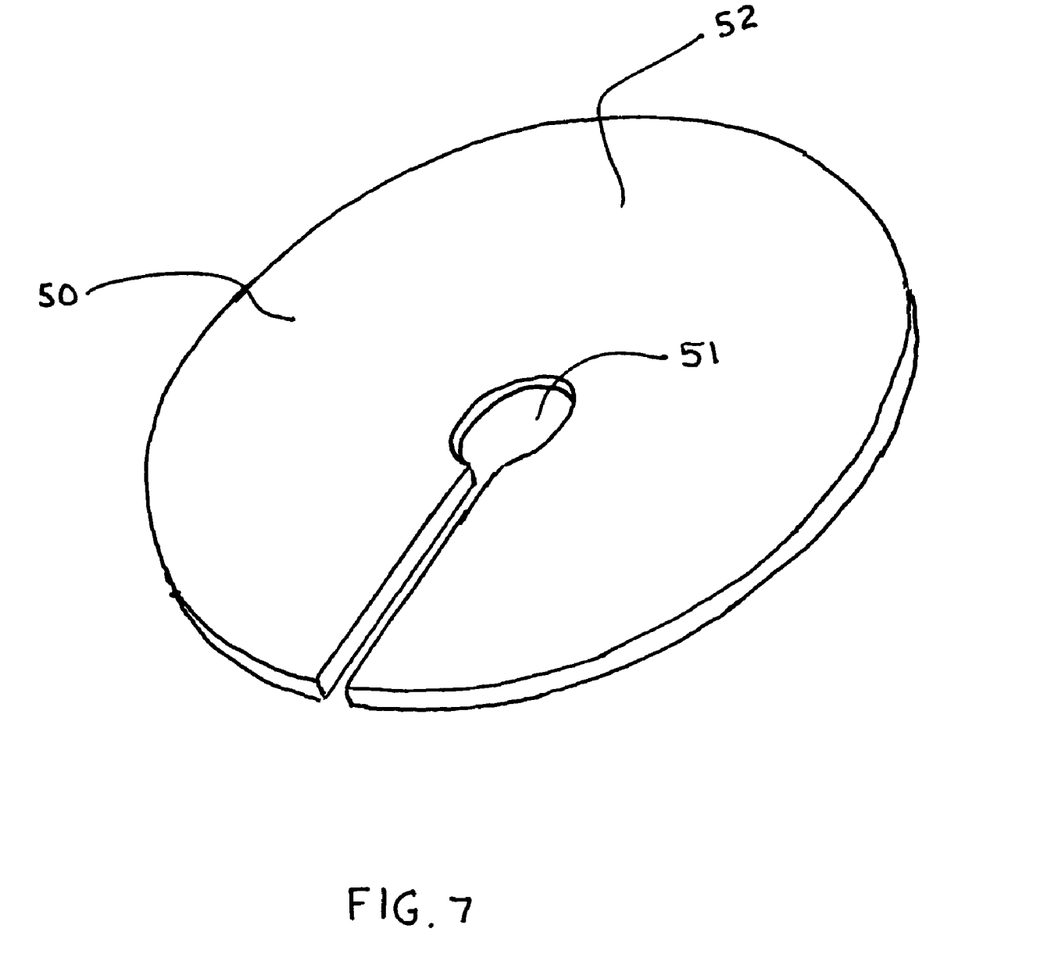
FIG. 7 depicts an illustrative view of the retainer of the FIG. 1 kit in greater detail.

FIG. 7 depicts a first embodiment of the retainer 50. The retainer 50 is provided so as to retain the anchor 20 in position. The retainer 50 is envisioned to have numerous possible configurations some of which will be discussed at greater length in this specification. In this first embodiment, the retainer 50 may be configured as a simple disc, washer, button, or ring. This retainer 50 could be provided with a through-hole or slot 51 for capturing a knot 28, depicted in FIG. 9, formed by tying off the shaft 23. The knot 28 would seat against an exterior facing surface 52 of the retainer 50.

One advantage gained by the use of such a retainer is that the retainer could be made as thin as possible, on the order of 1 to 2 mm, and in some cases dependent upon the material from which it is manufactured, even thinner. A retainer of this construction would have a very low profile and could easily be concealed by the application of a bandage over the skin of the patient. This would enable the anchor 20 to be in place, performing its function, yet not be noticeable to the public. This may provide a beneficial effect to the health and mental well-being of the patient as well as enable the patient to be more active in that little of the anchor 20 would protrude from the patient's body. Moreover, this would assist in maintaining sterility of the site, and may minimize the potential for inadvertent traumatic injury to the area.

Figure 8:
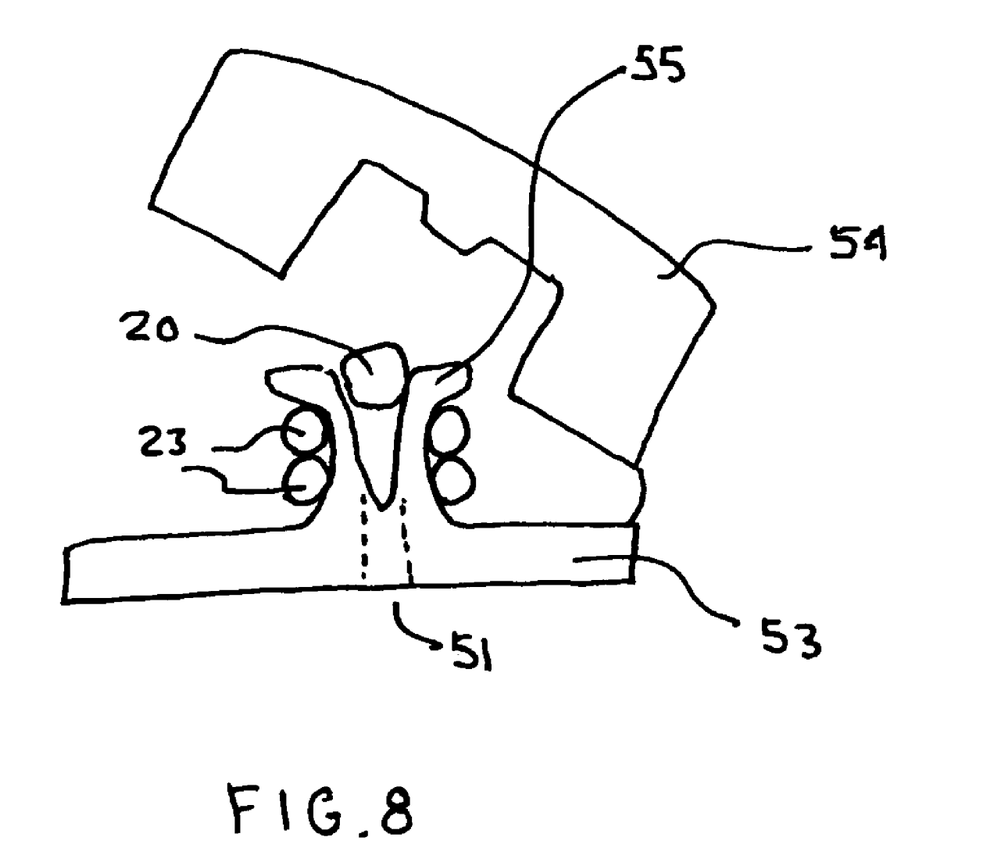
FIG. 8 depicts an illustrative view of an alternative embodiment of the FIG. 7 retainer.

In a second embodiment depicted in FIG. 8, a multicomponent design may be used to secure the anchor 20 in place. One example may utilize a base plate 53 for seating against the patient's body, and a lid or cap 54 secured to the cap to cover the base plate 53 as well as that portion of the anchor 20 protruding from the body. The base plate 53 may be configured similarly to the FIG. 7 retainer in that it would possess a slot 51 or central opening which would enable the base plate to secure the shaft 23. The shaft 23 may be pulled under tension and wedged or otherwise secured into the base plate 53, for example, by engaging the shaft 23 with a fixture 55 such as by passing the anchor 20 through the fixture 55 and wrapping the shaft 23 around the fixture to secure the shaft 23 in a manner reminiscent of tying a line to a cleat. This configuration may also be covered with a bandage as described above, or the cap 54 may be secured over the base plate 53. The base plate 53 and cap 54 configuration may be made to have a low profile. Such an arrangement may range in thickness from about 5 mm to about 15 mm in dimension as measured from a position normal to the abdomen of the patient.

A third embodiment of the retainer 50, may be similar to that depicted in U.S. patent application Ser. No. 11/139,927 filed on May 27, 2005 entitled "Clamp for Flexible Tube" which is copending and commonly assigned, the disclosure of which is herein incorporated by reference in its entirety.

Figure 9:
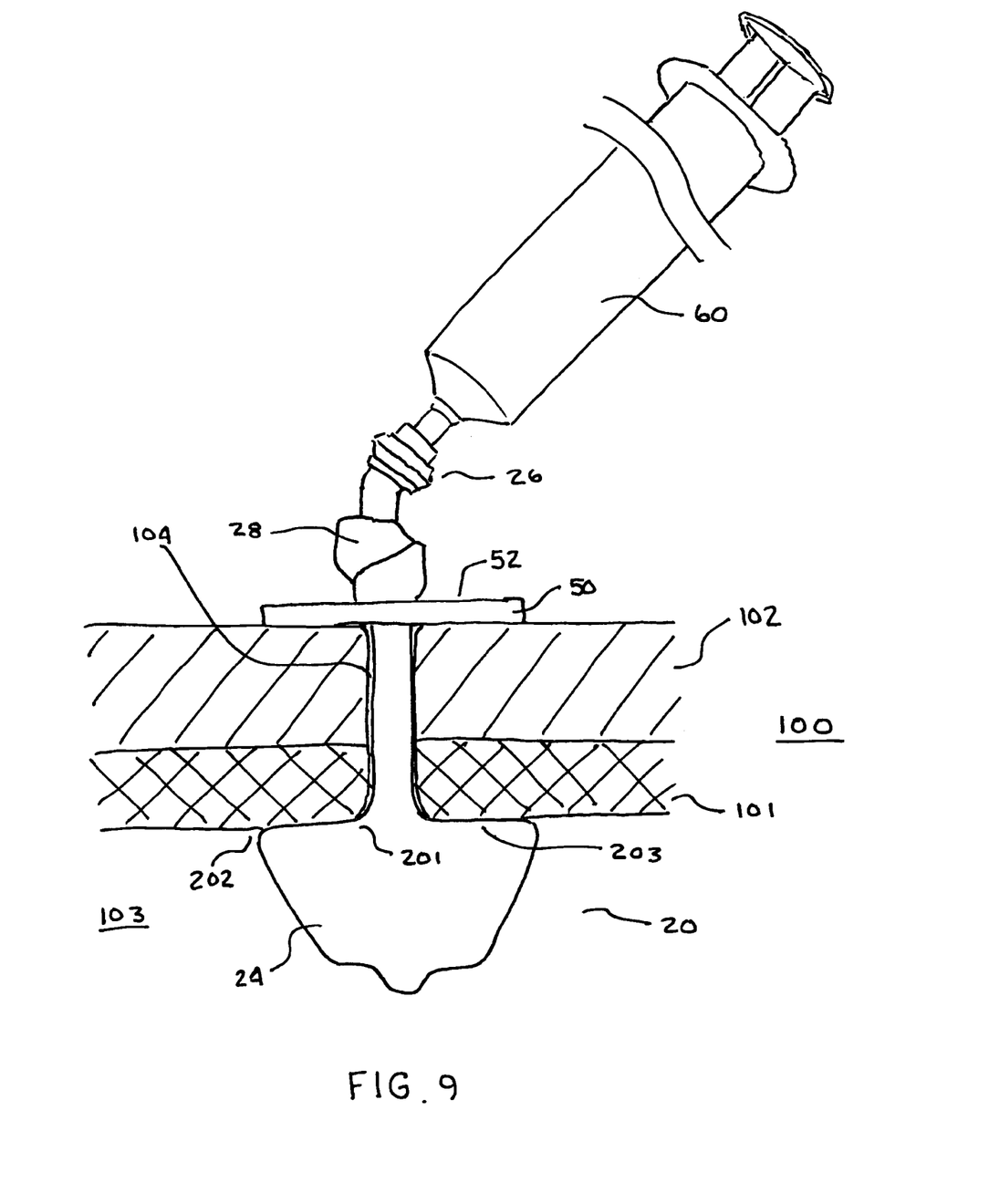
FIG. 9 depicts an illustrative view of the introducer of the FIG. 1 kit at a point in time when the anchor is in place in the procedure.

FIG. 9 depicts the anchor 20 in place within a body 100. As may be seen the inflator 60 is connected to the anchor 20 at the connector 26. Due to the small size of the anchor 20, the inflator 60 may simply be a syringe capable of injecting into as well as removing a fluid from the anchor 20. Although in many instances, the fluid is air, it should be understood that the ballooned region 24 may be inflated and deflated upon application or removal of other fluids, both gaseous and liquid, including but not limited to water and saline. In the FIG. 9 embodiment, it may be seen how the anchor 20 is used to secure the gastric wall 101 to the abdominal wall 102 by entering the patient's body 100 into the stomach or gastric lumen 103 through a stoma 104 created by the initial incision.

To better serve the purpose intended, additional desirable features may be incorporated into the ballooned region during the molding process which would prove useful in the application of the invention. For example, the ballooned region 24 may be preshaped so as to possess sufficiently small shoulder radii at regions 201 and 202 so that a face 203 may be created which is relatively flat in shape. This face would create a large resting or bearing surface to seat with the gastric wall 101. The surface area of the face 203 working in conjunction with inflation of the ballooned region 24 would help minimize the likelihood of the anchor 20 from slipping out of the stoma 104. Other desirable retention element shapes may be created as well, depending upon the application. For example, the overall geometry of the ballooned region 20 may be bullet-shaped, disc-shaped, spherical, cylindrical, frustoconical or any other suitable shape limited only by the purpose intended and the skill of those in the art at forming preshaped balloons.

As described above in more detail, once the anchor 20 is in place, the ballooned region 24 properly situated and inflated, in many embodiments, including that of FIG. 9, the proximal end 22 may simply be tied off. The reason that tying the anchor at the proximal end would be possible is due to the small size of the anchor and the low inflation pressures needed to fully inflate the anchor once it is in place. It is envisioned that the diameter of the shaft 23 in many embodiments may be as small as from about 0.8 mm to about to 1.5 mm, and the ballooned region 24 may be considered fully inflated at pressures as low as from about 50 mbar to about 200 mbar.

Other features that may be incorporated into any of the embodiments is to provide the anchor 20 with a lengthening feature. This may prove useful and assist in deployment of the anchor from the introducer. In such an embodiment, as the ballooned region 24 is inflated, inflation is first caused to extend the anchor longitudinally prior to any radial expansion of the ballooned region 24. Such a feature would enable the inflation process itself to deploy the ballooned region from the sheath. Once the ballooned region 24 had fully deployed from the introducer 30 and the likelihood of damage to the anchor 20 were minimized, the introducer may be withdrawn from the body in any of the fashions described above and the ballooned region may continue to be inflated sufficiently so as to secure the anchor in place. This controlled expansion may be accomplished by molding the ballooned region in a manner that will specifically cause it to deploy from the introducer, or by preloading the anchor within the introducer so that it will do the same. One possible technique which may be used is to preload the introducer with the anchor, but to twist the anchor torsionally during the loading process and bunch up a portion of the anchor within the introducer. The twist would occlude the passage of the inflation fluid but would cause the anchor to move until such time as the twist were to clear the introducer. At that time, the anchor would untwist allowing the ballooned region to expand. Obviously folding the anchor without twisting may be made to accomplish the same effect.

Due to the controllable collapsibility of the anchor 20 it would be more amenable to atraumatic removal from the stoma than are prior art devices. This is because the present invention does not require the significant trans-abdominal exertion typically associated with those prior art devices containing a rigid shaft for carrying the balloon component. In the prior art devices, the mechanics of the balloon member are typically altered negatively over time, for example, balloon members associated with the prior art are known to stiffen and lose their ability to retract fully into the shaft completely. This results in the creation of traumatizing folds that may exacerbate healing of the stoma site upon removal or subsequent manipulation of the catheter. Proper selection of materials will prevent the present invention from exhibiting such features.

In many of these procedures, a plurality of anchors are used in close proximity to one another. For example, in one gastropexy procedure, often three or four anchors are used in conjunction with one another. Once the stomach wall and the abdominal wall are secured to one another, a gastrostomy tube is often placed into the stomach lumen by making an additional incision at a location interior to the perimeter of the plurality of gastropexy devices. In any event, an individual retainer may be made to have the capability of securing more than one anchor 20 therein. That is, a single retainer may be used to secure two or more of the devices described above, so long as the devices were sufficiently closely spaced to one another.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

I claim:

1. A percutaneous gastrointestinal anchoring kit comprising:
   an anchor having a ballooned region at a distal end of the anchor and a shaft portion extending from the ballooned region to a proximal end of the anchor, both the ballooned region and the shaft manufactured of a hollow, collapsible, homogeneous polymeric material, the material in the ballooned region being substantially thinner in wall thickness than the material in the shaft portion;
   an introducer for traversing body tissue layers from an exterior surface of a patient body to a gastric lumen interior to the patient body, the introducer adapted to insert and deploy the anchor within the patient body;
   a guide for positioning at least the ballooned region of the anchor from the introducer into the gastric lumen while enabling at least the proximal end of the anchor to be manipulable at the exterior surface of the patient body;
   an inflator for cooperating with the proximal end of the anchor for introducing a fluid into or removing a fluid out of the anchor so as to selectively inflate or deflate the ballooned region within the gastric lumen; and
   a retainer for securing the anchor within the gastric lumen when the ballooned region is inflated, the retainer adapted to be seated against the exterior surface of the patient body for capturing and securing the proximal end of the anchor and for placing a tractive force on the ballooned region so as to pull the gastric lumen to an interior abdominal wall of the patient body, the retainer including a base plate and a cap adapted to be positioned on the exterior surface such that a portion of the anchor protruding from the stoma is positioned through a slot on a proximal surface of the base and the portion of the anchor in the slot is crimped closed by a protuberance on the cap which is positioned in the slot and against the portion of the anchor when the cap is positioned in a closed position against the base.

2. The percutaneous gastrointestinal anchoring kit of claim 1 wherein the anchor comprises polyurethane, and wherein the ballooned region is preshaped so as to possess a flattened bearing surface for contacting the gastric lumen when the ballooned region is inflated.

3. The percutaneous gastrointestinal anchoring kit of claim 2 wherein the anchor comprises a tip distal to the ballooned region.

4. The percutaneous gastrointestinal anchoring kit of claim 1 wherein the anchor comprises a connector at the proximal end for attachable and detachable interaction with the inflator.

5. The percutaneous gastrointestinal anchoring kit of claim 1 wherein a portion of the anchor is bent at an angle and positioned through the slot.

6. The percutaneous gastrointestinal anchoring kit of claim 1 wherein the introducer comprises a needle adapted to make the initial penetration through the body tissue layers and into the gastric lumen.

7. The percutaneous gastrointestinal anchoring kit of claim 6 wherein at least a portion of the introducer is longitudinally splittable and removable in at least two longitudinally discrete parts.

8. The percutaneous gastrointestinal anchoring kit of claim 6 wherein the introducer comprises a slotted distal end, the slot for capturing a portion of the anchor and pushing it through the body tissue layers into the gastric lumen prior to deployment.

9. The percutaneous gastrointestinal anchoring kit of claim 1 wherein the guide comprises a rod attached to the distal end of the anchor, extending along the shaft and terminating near the proximal end of the anchor, the rod adapted to transfer movement from the proximal end of the anchor to the distal end of the anchor so as to effect a movement in the ballooned region.

10. The percutaneous gastrointestinal anchoring kit of claim 9 wherein the rod is situated internal to the anchor and has a cross sectional area of between about one-third to about two-thirds of a cross sectional area of an inside diameter of the shaft portion of the anchor.

11. The percutaneous gastrointestinal anchoring kit of claim 1 comprising a tray for containment of the articles enumerated.

* * * * *

UNITED STATES PATENT AND TRADEMARK OFFICE
CERTIFICATE OF CORRECTION

PATENT NO.        : 7,582,098 B2                                              Page 1 of 1
APPLICATION NO.   : 11/510888
DATED             : September 1, 2009
INVENTOR(S)       : Fred Göbel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 255 days.

Signed and Sealed this

Fourteenth Day of September, 2010

David J. Kappos
*Director of the United States Patent and Trademark Office*